United States Patent
Madden et al.

(10) Patent No.: US 11,817,185 B2
(45) Date of Patent: Nov. 14, 2023

(54) STABLE LABEL ISOTOPE TRACING FOR UNTARGETED DATA

(71) Applicant: Agilent Technologies, Inc., Santa Clara, CA (US)

(72) Inventors: Stephen P. Madden, Campbell, CA (US); Steven M. Fischer, Hayward, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 799 days.

(21) Appl. No.: 16/846,185

(22) Filed: Apr. 10, 2020

(65) Prior Publication Data

US 2020/0365237 A1    Nov. 19, 2020

Related U.S. Application Data

(60) Provisional application No. 62/834,041, filed on Apr. 15, 2019.

(51) Int. Cl.
| | |
|---|---|
| *G16C 20/30* | (2019.01) |
| *G16C 20/70* | (2019.01) |
| *G16C 20/50* | (2019.01) |
| *G16H 10/40* | (2018.01) |

(52) U.S. Cl.
CPC ............ *G16C 20/30* (2019.02); *G16C 20/50* (2019.02); *G16C 20/70* (2019.02); *G16H 10/40* (2018.01)

(58) Field of Classification Search
CPC ........ G16H 20/17; G16H 50/20; G16H 10/40; G16C 20/30; G16C 20/50; G16C 20/70

USPC .......................................................... 702/19
See application file for complete search history.

(56) References Cited

U.S. PATENT DOCUMENTS

2020/0312436 A1* 10/2020 Kuchimanchi et al. ..................... G16H 20/17

OTHER PUBLICATIONS

Agilent Technologies, Inc; Batch Processing Software for High Quality Feature Extraction of Mass Spectrometry Data; Feb. 14, 2014; pp. 1-12.
Agilent Technologies, Inc; Solving the Challenge of Isotopologue Extraction for Qualitative Flux Analysis; Apr. 14, 2016; pp. 1-6.
Chokkathukalam, Achuthanunni et al.; Stable Isotope-Labeling Studies in Metabolomics; New Insights Into Structure and Dynamics of Metabolic Networks; Feb. 2014; pp. 1-23.

(Continued)

*Primary Examiner* — Thinh T Nguyen
(74) *Attorney, Agent, or Firm* — Mannava & Kang, P.C.

(57) ABSTRACT

A method for analyzing samples utilizing stable label isotope tracing includes receiving mass spectrometry (MS) data generated by an MS system performing untargeted data acquisition on a plurality of samples, performing untargeted feature extraction on the unlabeled compound data to generate a data set of first extracted features, generating a plurality of empirical molecular formulas respectively corresponding to the first extracted features, performing targeted isotopologue extraction on the labeled compound data to generate a data set of second extracted features, wherein the targeted isotopologue extraction is based on the empirical molecular formula and retention time of each first extracted feature, and identifying one or more groups of isotopologues from the second extracted features.

20 Claims, 8 Drawing Sheets

(56) References Cited

OTHER PUBLICATIONS

Tamerly Timothy et al.; Untargeted Metabolomics Studies Employing NMR and LC-MS Reveal Metabolic Coupling Between Nanoarcheum Equitans and its Archael host Ignicoccus Hospitals; Aug. 1, 2015; pp. 1-24.
Huang, Xiaojing et al.; X13 CMS: Global Tracking of Isotopic Labels in Untargeted Metabolomics; Jan. 7, 2014; pp. 1-8.
Roberts, Lee D. et al.; Targeted Metabolomics; Apr. 2012; pp. 1-34.
Tautenhahn, Ralf et al.; An Accelerated Workflow for Untargeted Metabolomics Using the METLIN Database; Sep. 2012, pp. 1-6.
Agilent Technologies "MassHunter Profinder Software—Quick Start Guide"; Agilent Technologies, Inc; Sep. 30, 2017; pp. 1-48.
Agilent Technologies "MassHunter VistaFlux Software—Workflow Guide"; Agilent Technologies, Inc; May 31, 2016; pp. 1-146.
Baumeister, Tim U. H. et al; "DeltaMS: A Tool to Track Isotopologues in GC- and LC-MS Data"; Metabolomics, Springer New York LLC, US; vol. 14 No. 4; Feb. 27, 2018; pp. 1-10.
Extended European Search Report dated Aug. 13, 2020 for Application No. 20167578.2; EPO; pp. 1-14.
Weindl, Daniel et al; "Isotopologue Ratio Normalization for Non-Targeted Metabolomics"; Journal of Chromatography A, vol. 1389; Feb. 17, 2015; pp. 112-119.
Yuqin, Dai et al; "Metabolomics Batch Data Analysis Workflow to Characterize Differential Metabolites in Bacteria Application"; Agilent Techologies, Inc; Apr. 18, 2015; pp. 1-8.

* cited by examiner

STABLE LABEL ISOTOPE TRACING FOR UNTARGETED DATA

RELATED APPLICATIONS

This application claims the benefit under 35 U.S.C. § 119(e) of U.S. Provisional Patent Application Ser. No. 62/834,041, filed Apr. 15, 2019, titled "STABLE LABEL ISOTOPE TRACING FOR UNTARGETED DATA," the content of which is incorporated by reference herein in its entirety.

TECHNICAL FIELD

The present invention relates generally to stable label isotope tracing utilized in conjunction with mass spectrometry (MS), for untargeted data acquisition, processing, and analysis.

BACKGROUND

Isotope tracing refers to techniques utilized to track the passage or fate of an isotope through a (bio)chemical reaction or series of reactions, one example being a metabolic pathway in the case of a metabolic process occurring in a biological cell. A chemical or biological compound can be isotopically labeled (or marked) by purposely replacing an atom(s) of the compound with an atom that is the same element as, but a different isotope than, the original atom. For example, an isotopically labeled organic molecule may be formed by replacing one or more carbon-12 ($^{12}C$) atoms of the molecule with carbon-13 ($^{13}C$) atoms. The labeled compound is then subjected to, or allowed to undergo, the reaction(s) of interest. The product compounds of the reaction, including the position(s) and patterns of the isotope in the product compounds, may then be measured to obtain information, such as the sequence or pathway taken by the isotope through the reaction to get to the observed compound(s). Depending on the type of analysis being made, the reaction products of the isotopically labeled starting compound may be compared to the reaction products of the unlabeled counterpart. "Stable" isotopes refer to non-radioactive isotopes (i.e., not involving radionuclides). Stable isotopes commonly utilized in isotope tracing include carbon-13 ($^{13}C$), nitrogen-15 ($^{15}N$), and deuterium ($^{2}H$), however any element with more than one stable isotope can be used for isotope tracing experiments.

One technique utilized to measure stable label isotopes is mass spectrometry (MS). In general, an MS system includes an ion source for ionizing the components of a sample under investigation (including an isotopically labeled compound), a mass analyzer for separating the resulting ions based on their differing mass-to-charge ratios (or m/z ratios, or more simply "masses"), an ion detector for counting the separated ions, and electronics for processing output signals from the ion detector as needed to produce user-interpretable data in a format such as a chromatogram or a mass spectrum. Typically, the mass spectrum is a series of peaks indicative of the relative abundances of detected ions (e.g., ion signal intensity such as number of ion counts for each ion detected) as a function of their m/z ratios. The mass spectrum or MS/MS fragment spectrum may be utilized to determine the molecular structures of components of the sample, thereby enabling the sample to be qualitatively and quantitatively characterized, including the identification of, abundance of, distribution of, and differences between isotopologues and isotopomers for each compound found in the analysis. Mass spectrometry, when applied to biological processes, therefore may be utilized for quantitative metabolic flux analysis (MFA or qualitative flux analysis (stable isotope tracing).

The mass spectrometry technique may be enhanced by coupling it with another analytical separation technique that precedes the MS analysis stage. Examples include chromatographic techniques such as liquid chromatography (LC) or gas chromatography (GC). In an LC system, for example, a mobile phase consisting of one or more solvents is driven using pressure through a chromatography column. The LC column contains a stationary phase, which in LC is typically provided in the form of a packed bed of particles such as, for example, chemically modified porous silica beads. The particles are formulated and/or functionalized so as to separate different components (e.g., chemical compounds) of a sample. The sample to be processed by the LC system is injected into the mobile phase at a point upstream of the column. The sample is then transported with the mobile phase through the column by the flow created by the high system pressure. As the sample flows though the column, the sample contacts the stationary phase. The different components of the sample have different affinities for the stationary phase. This causes the different components to separate from each other in the liquid flow though the column. Consequently, the different components elute from the column outlet at different times. Hence, the flow of liquid outputted from the column contains a series of bands, each band consisting of a distinct component of the sample. That is, the bands respectively consist of the different components of the sample that were separated from each other by the column. In a GC system, the mobile phase is a carrier gas that carries a gas-phase sample through a GC column in which the stationary phase may be an inside lining of the column. Additionally, techniques other than LC or GC may be utilized as the first stage of analytical separation, such as electrophoretic-based techniques, for example capillary electrophoresis (CE).

In a hybrid LC/MS, GC/MS, or CE/MS system, the separated compounds eluting from the column or electrophoretic instrument (e.g., a CE capillary) are introduced into the ion source of the MS system, and the MS system processes the separated compounds as summarized above. A hybrid MS system can combine the advantages of the first-stage analytical separation technique (e.g., LC, GC, or CE) and the second-stage analytical separation technique (MS). For example, a hybrid MS system is capable of acquiring three-dimensional (3D) LC/MS, GC/MS, or CE/MS data from a sample, characterized by retention time (or elution time or acquisition time), ion abundance, and m/z as sorted by the MS system. The multi-dimensional MS data is useful for measuring and discriminating among the different compounds of complex samples. For example, two different compounds may co-elute from a chromatography column at about the same time, but because they have different masses they can be subsequently separated by the MS system to avoid overlapping peaks in the data, assuming the MS system operates at sufficient resolution.

A sample analysis utilizing MS-based stable label isotope tracing traditionally has been a targeted, or biased, analysis in which a limited number of known compounds are measured. More recently, untargeted (unbiased) approaches to analyzing samples containing unknown compounds are being investigated to expand the analytical capabilities of MS-based stable label isotope tracing and produce more comprehensive information.

One example of an untargeted approach is the use of $X^{13}CMS$ software. See Huang et al., $X^{13}CMS$: Global Tracking of Isotopic Labels in Untargeted Metabolomics, *Anal. Chem.*, 86, p. 1632-1639, American Chemical Society (2014). The $X^{13}CMS$ software analyzes data acquired from an unlabeled sample and a labeled sample run through an LC/MS system. The $X^{13}CMS$ software finds feature groups in the unlabeled and labeled samples in an untargeted fashion. In the present context, a "feature group" is the set of ions at a given retention time that are isotope clusters. The $X^{13}CMS$ software then compares the feature groups to look for isotopologue differences. However, known untargeted data analyzing techniques such as implemented by the $X^{13}CMS$ software can operate slowly and produce erroneous results such as isotope gaps and incorrect isotope clustering, and may be unable to find isotope incorporations that are stochastic rather than continuous.

Therefore, there is a need for improved methods and systems for stable label isotope tracing for untargeted data.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for analyzing samples utilizing stable label isotope tracing includes: (a) receiving mass spectrometry (MS) data generated by an MS system performing untargeted data acquisition on a plurality of samples, wherein: the plurality of samples comprise an unlabeled sample containing unlabeled compounds, and a labeled sample containing isotopically labeled compounds and being chemically or biologically equivalent to the unlabeled sample; the MS data comprise unlabeled compound data and labeled compound data; the unlabeled compound data comprise retention time data, mass-to-charge ratio (m/z) data, and abundance data corresponding to molecular features of the unlabeled sample detected by the MS system; and the labeled compound data comprise retention time data, m/z data, and abundance data corresponding to molecular features of the labeled sample detected by the MS system; (b) performing untargeted feature extraction on the unlabeled compound data to generate a data set of first extracted features; (c) generating a plurality of empirical molecular formulas respectively corresponding to the first extracted features; (d) performing targeted isotopologue extraction on the labeled compound data to generate a data set of second extracted features, wherein the targeted isotopologue extraction is based on the empirical molecular formula and retention time of each first extracted feature; and (e) identifying a stable label incorporated compound by observing changes in isotopologue pattern from natural in the second extracted features.

According to another embodiment, a system for analyzing samples utilizing stable label isotope tracing includes: a controller configured to receive MS data and control or perform all or part of any of the methods disclosed herein.

According to another embodiment, a non-transitory computer-readable storage medium includes instructions for performing all or part of any of the methods disclosed herein.

According to another embodiment, a system includes the computer-readable storage medium.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1A:
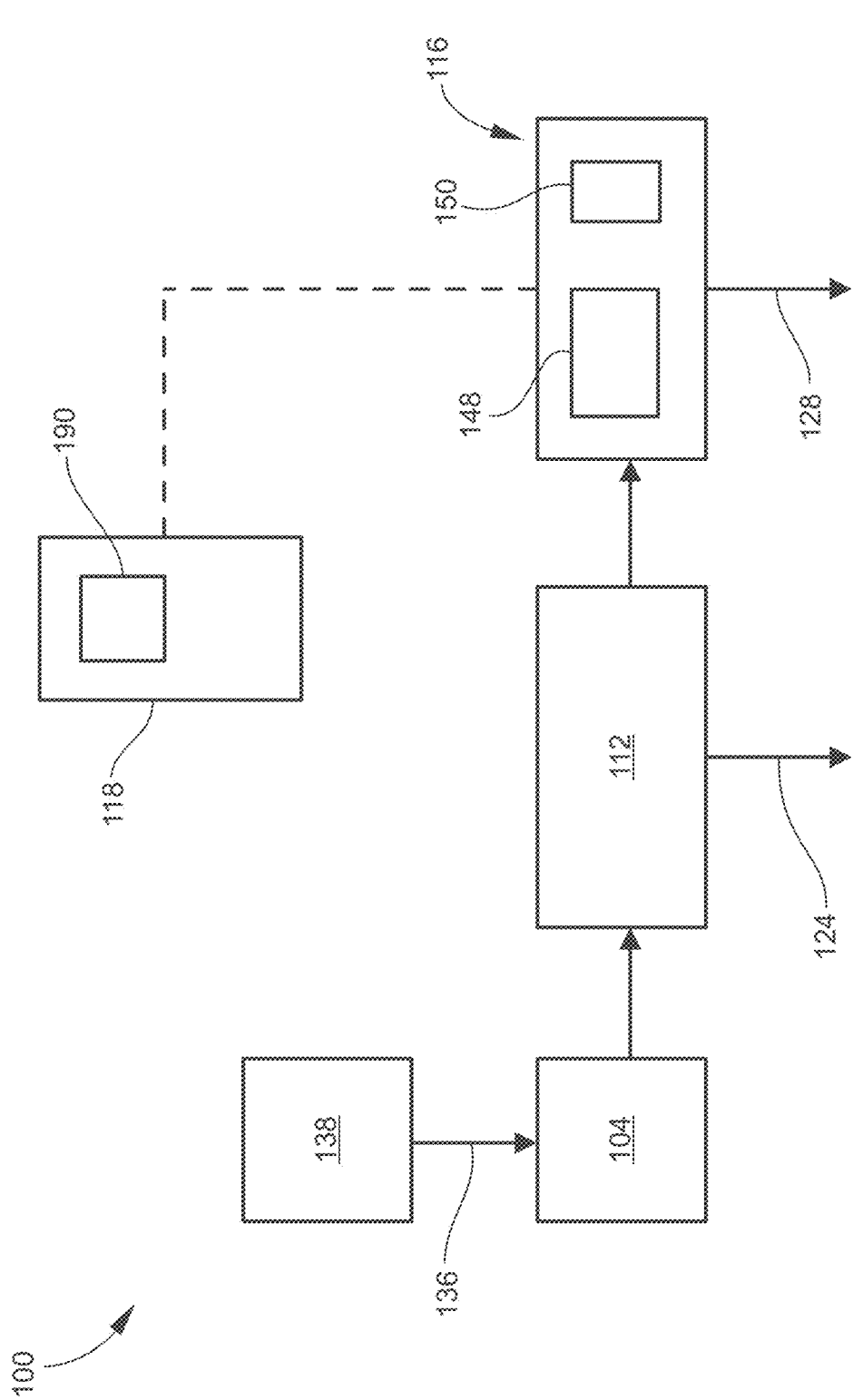
FIG. 1A is a schematic view of an example of a mass spectrometry (MS) system according to an embodiment, which may be utilized in the implementation of the subject matter described herein.

FIG. 1A is a schematic view of an example of a mass spectrometry (MS) system 100 according to an embodiment, which may be utilized in the implementation of the subject matter described herein. The operation and design of various components of MS systems are generally known to persons skilled in the art and thus need not be described in detail herein. Instead, certain components are briefly described to facilitate an understanding of the subject matter presently disclosed.

The MS system 100 may generally include an ion source 104, a mass spectrometer (MS) 116, and a computing device (or computer, or system controller) 118. In some embodiments, the spectrometry system 100 may also include an intermediate ion processing section 112 generally serving as an interface (or an intermediate section or region) between the ion source 104 and the MS 116. Generally, the ion processing section 112 may be representative of one or more ion processing components (structures, devices, regions, etc.) positioned between the ion source 104 and the MS 116. These components may serve various functions such as, for example, pressure reduction, neutral gas removal, ion trapping/gating, ion beam focusing/guiding, ion mass filtering/selection, ion fragmentation, etc. Examples of intermediate components include, but are not limited to, ion optics, ion traps, multipole ion guides, stacked-ring ion guides, drift cells, collision cells, ion funnels, etc., as appreciated by persons skilled in the art. The ion processing section 112 may include a housing enclosing one or more chambers. Each chamber may include one or more such components.

The MS system 100 also includes a vacuum system for maintaining various interior regions or chambers of the MS system 100 at controlled, sub-atmospheric pressure levels. The vacuum system is schematically depicted by vacuum lines 124 and 128. The vacuum lines 124 and 128 are schematically representative of one or more vacuum-generating pumps and associated plumbing and other components appreciated by persons skilled in the art. The vacuum lines 124 and 128 may also remove any residual non-analytical neutral molecules from the ion path through the MS system 100.

The ion source 104 may be any type of continuous-beam or pulsed ion source suitable for producing analyte ions for spectrometry. In a typical embodiment, the ion source 104 is an electrospray ionization (ESI) source. However, other types of ion sources may be utilized depending on the configuration of the MS system 100, the sample to be analyzed, the analytical separation instrument coupled to the ion source 104, etc. Examples of other ion sources 104 include, but are not limited to, other types of spray-type devices (e.g., thermospray ionization devices, sonic spray devices, etc.), other types of atmospheric pressure ionization (API) sources, photo-ionization (PI) sources, electron ionization (EI) sources, chemical ionization (CI) sources, field ionization (FI) sources, plasma or corona discharge sources, fast atom bombardment (FAB) sources, laser desorption ionization (LDI) sources, and matrix-assisted laser desorption ionization (MALDI) sources. In some embodiments, the ion source 104 may include two or more ionization devices, which may be of the same type or different type. Depending on the type of ionization implemented, the ion source 104 may reside in a vacuum chamber or may operate at or near atmospheric pressure. Sample material to be analyzed may be introduced to the ion source 104 by any suitable means, including hyphenated techniques in which the sample material is an output 136 of an analytical separation instrument 138 such as, for example, a liquid chromatography (LC) instrument, gas chromatography (GC) instrument, capillary electrophoresis (CE) instrument, etc.

The MS 116 may generally include a mass analyzer 148 and an ion detector 150 enclosed in a housing. The vacuum line 128 maintains the interior of the MS 116 at very low (vacuum) pressure (e.g., ranging from $10^{-4}$ to $10^{-9}$ Torr). The mass analyzer 148 separates analyte ions on the basis of their different mass-to-charge (m/z) ratios. In some embodiments, the mass analyzer 148 is a time-of-flight (TOF) analyzer. A TOF analyzer includes an ion pulser (or extractor) and a generally electric field-free flight tube. Entrance optics direct the ion beam into the ion pulser, which pulses the ions into the flight tube as ion packets. The ions drift through the flight tube toward the ion detector 150. Ions of different masses travel through the flight tube at different velocities and thus have different overall times-of-flight, i.e., ions of smaller masses travel faster than ions of larger masses. Each ion packet spreads out (is dispersed) in space in accordance with the time-of-flight distribution. The ion detector 150 detects and records the time that each ion arrives at (impacts) the ion detector 150. A data acquisition process of the computing device 118 correlates the recorded times-of-flight with m/z ratios.

More generally, various types of mass analyzers other than a TOF analyzer may be utilized in the MS system 100. Examples include, but are not limited to, multipole electrode structures (e.g., quadrupole mass filters, linear ion traps, three-dimensional Paul traps, etc.), electrostatic traps (e.g. Kingdon, Knight and ORBITRAP® traps), ion cyclotron resonance (ICR) or Penning traps (such as utilized in Fourier transform ion cyclotron resonance mass spectrometry (FT-ICR or FTMS)), electric field sector instruments, magnetic field sector instruments, etc.

The ion detector 150 may be any device configured for collecting and measuring the flux (or current) of mass-discriminated ions outputted from the mass analyzer 148. Examples of ion detectors 150 include, but are not limited to, multi-channel plates (MCPs), electron multipliers (Ems), photomultipliers, and Faraday cups.

In some embodiments, the MS 116 in combination with the ion processing section 112 may form a tandem MS or $MS^n$ system. As an example, the ion processing section 112 may include an ion guide configured as a quadrupole mass filter for selecting ions of a specific m/z or m/z range, and another multipole ion guide configured as a non-mass-resolving, radio-frequency (RF)-only collision cell for producing fragment ions. In the collision cell, ions collide with a collision gas (e.g., argon, nitrogen, helium, etc.). The gas pressure is high enough to enable ions that collide with the gas molecules (with sufficient energy) to fragment into less massive ions by the mechanism known as collision-induced dissociation (CID). The fragment ions are then transferred into the mass analyzer 148.

An ion fragmentation device if provided in the MS system 100 may have a configuration other than a CID-based device. For example, the ion fragmentation device may be configured to perform electron capture dissociation (ECD), electron transfer dissociation (ETD), infrared multiphoton dissociation (IRMPD), etc.

As appreciated by persons skilled in the art, a spectrometry system as disclosed herein may include various other ion optics positioned along the ion path that are not specifically described above or shown in the drawing figures. Such ion optics may be configured for controlling or manipulating (e.g., focusing, shaping, steering, cooling, accelerating, decelerating, slicing, etc.) the ion beam, as appreciated by persons skilled in the art.

The computing device (or system controller, or controller) 118 is schematically depicted as representing one or more modules (or units, or components) configured for controlling, monitoring and/or timing various functional aspects of the MS system 100 such as, for example, the upstream analytical separation instrument 138, ion source 104, one or more components of the ion processing section 112, and the MS 116, as well as any vacuum pumps, ion optics, sample introduction device, etc., that may be provided in the MS system 100 but not specifically shown in FIG. 1A. One or more modules (or units, or components) may be, or be embodied in, for example, a desktop computer, laptop computer, portable computer, tablet computer, handheld computer, mobile computing device, personal digital assistant (PDA), smartphone, etc. The computing device 118 may also schematically represent all voltage sources not specifically shown, as well as timing controllers, clocks, frequency/waveform generators and the like as needed for applying voltages to various components of the MS system 100. The computing device 118 may also be configured for receiving the ion detection signals from the ion detector 150 and performing tasks relating to data acquisition and signal analysis as necessary to generate chromatograms, drift spectra, and mass (m/z) spectra characterizing the sample under analysis. The computing device 118 may also be configured for providing and controlling a user interface that provides screen displays of spectrometric data and other data with which a user may interact. The computing device 118 may include one or more reading devices on or in which a non-transitory computer-readable (machine-readable) medium may be loaded that includes instructions for performing all or part of any of the methods disclosed herein. For all such purposes, the computing device 118 may be in signal communication with various components of the MS system 100 via wired or wireless communication links (as partially represented, for example, by a dashed line between the computing device 118 and the MS 116.

The computing device 118 may include a data analyzer 190 (or data analyzing module, unit, or component) configured to analyze MS data produced by the MS system 100 according to any of the methods disclosed herein. Alternatively, the data analyzer 190 may be a separate component (such as may be embodied in a separate computing device) that communicates with the computing device 118 to receive MS data therefrom via a wired or wireless communication link, or is otherwise configured to receive and read the MS data in a non-transitory format such as may be stored in a memory or drive. Generally, the computing device 118 and the data analyzer 190, may include or be embodied in one or more types of hardware, firmware and/or software, as well as one or more memories and databases.

Figure 1B:
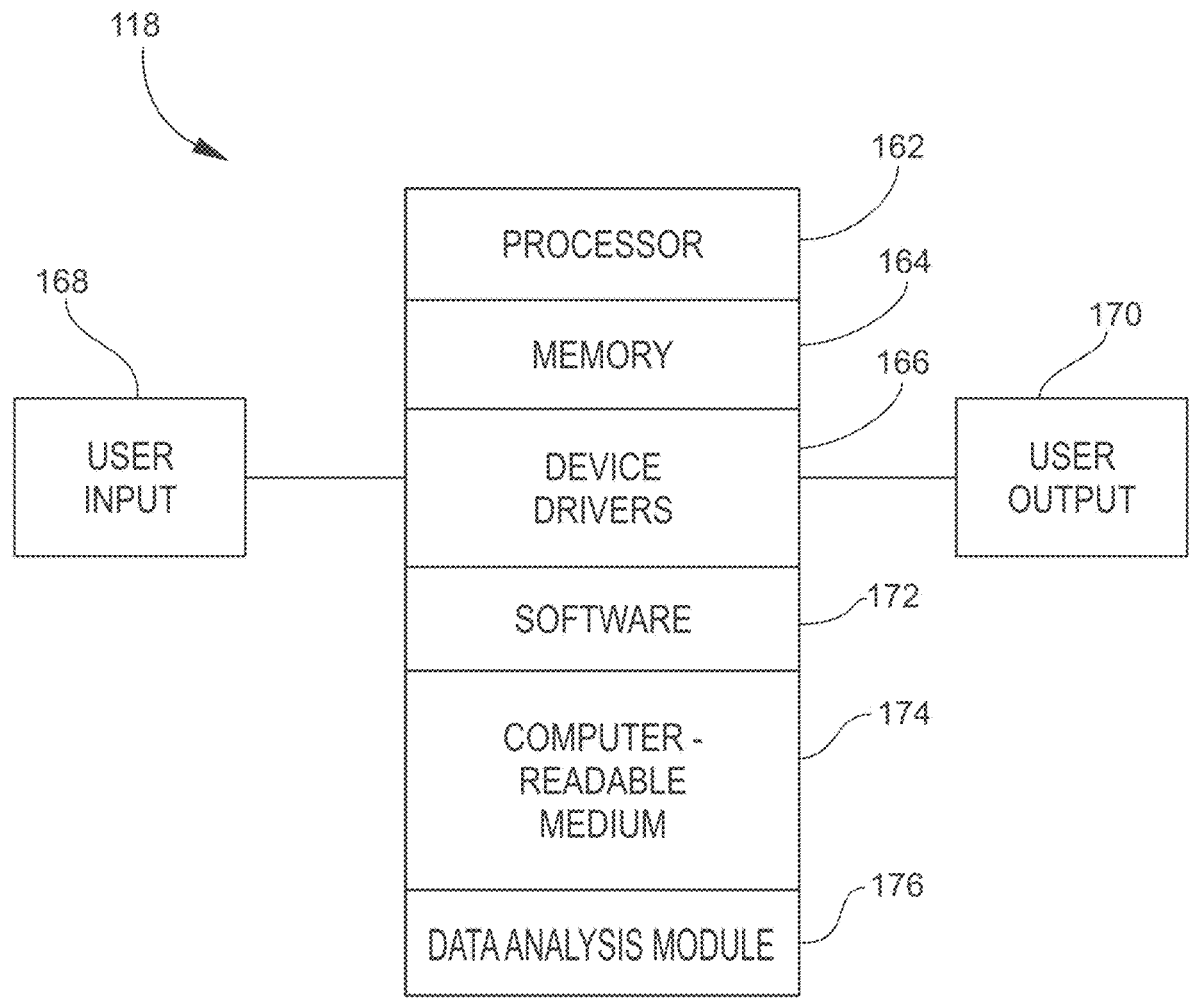
FIG. 1B is a schematic view of an example of a computing device or data analyzer that may be utilized in the implementation of the subject matter described herein.

FIG. 1B is a schematic view of an example of a data analyzer 190 or computing device that may be utilized in the implementation of the subject matter described herein. The data analyzer 190 may be part of the computing device 118 described above in conjunction with FIG. 1A, or may be (or be part of) a device separate or remote from such computing device 118. Accordingly, one or more components illustrated in FIG. 1B described herein as being part of data analyzer 190 may alternatively or additionally be shared with or part of the computing device 118. In the illustrated embodiment, the data analyzer 190 includes an electronics-based processor 162, which may be representative of a main electronic processor providing overall control, and one or more electronic processors configured for dedicated control operations or specific signal processing tasks (e.g., a graphics processing unit or GPU, a digital signal processor or DSP, an application-specific integrated circuit or ASIC, a field-programmable gate array or FPGA, etc.). The data analyzer 190 also includes one or more memories 164 (volatile and/or non-volatile) for storing data and/or software. The data analyzer 190 may also include one or more device drivers 166 for controlling one or more types of user interface devices and providing an interface between the user interface devices and components of the data analyzer 190 communicating with the user interface devices. Such user interface devices may include user input devices 168 (e.g., keyboard, keypad, touch screen, mouse, joystick, trackball, and the like) and user output devices 170 (e.g., display screen, printer, visual indicators or alerts, audible indicators or alerts, and the like). In various embodiments, the data analyzer 190 may be considered as including one or more user input devices 168 and/or user output devices 170, or at least as communicating with them. The data analyzer 190 may also include one or more types of computer programs or software 172 contained in memory and/or on one or more types of computer-readable media 174. The computer programs or software may contain instructions (e.g., logic instructions) for performing all or part of any of the methods for analyzing samples disclosed herein. The computer programs or software may also include application software and system software. System software may include an operating system (e.g., a Microsoft Windows® operating system) for controlling and managing various functions of the data analyzer 190, including interaction between hardware and application software. In particular, the operating system may provide a graphical user interface (GUI) displayable via a user output device 170 such as a display screen, and with which a user may interact with the use of a user input device 168 such as a keyboard or a pointing device (e.g., mouse). The data analyzer 190 may also include one or more data analyzer modules 176 (as may be embodied in hardware, firmware and/or software, including algorithms) configured specifically for performing one or steps of the methods for analyzing samples disclosed herein.

It will be understood that FIGS. 1A and 1B are high-level schematic depictions of an example of an MS system 100 and associated computing device 118 and data analyzer 190 consistent with the present disclosure. Other components, such as additional structures, vacuum pumps, gas plumbing, ion optics, ion guides, electronics, and computer-related or electronic processor-related components may be included as needed for practical implementations. It will also be understood that the computing device 118 and data analyzer 190 are schematically represented in FIGS. 1A and 1B as functional blocks intended to represent structures (e.g., circuitries, mechanisms, hardware, firmware, software, etc.) that may be provided. The various functional blocks and signal links have been arbitrarily located for purposes of illustration only and are not limiting in any manner. Persons skilled in the art will appreciate that, in practice, the functions of the computing device 118 and data analyzer 190 may be implemented in a variety of ways and not necessarily in the exact manner illustrated in FIGS. 1A and 1B and described herein.

In operation, a chemical or biological sample is introduced into the MS system 100 by first inputting the sample into the analytical separation instrument 138. The analytical separation instrument 138 performs the first dimension or stage of analytical separation, separating the sample into constituent chemical or biological compounds according to the operating principle of the analytical separation instrument 138 (chromatography, electrophoresis, etc.). Compounds separated from each other elute from the analytical separation instrument 138 as an output 136 at different retention times (or elution times). Different compounds elute at different times and thus have different detectable retention times. Certain groups of compounds may be different from each other yet nonetheless co-elute at about the same time, i.e., within the same retention time window. Co-eluting compounds may be further resolved by the MS 116, which performs the second dimension or stage of analytical separation. Accordingly, the compounds outputted from the analytical separation instrument 138 are subsequently introduced into the ion source 104. The ion source 104 ionizes the compounds, i.e., forms analyte ions from the compounds. The analyte ions may then be subjected to processing steps in the ion processing section 112 as appropriate for the method, and then transmitted into the mass analyzer 148. The mass analyzer 148 separates the received analyte ions by m/z (or flight time, depending on the embodiment), and the separated ions then arrive at the ion detector 150. The ion detector 150 records the times at which it receives the mass-separated ions and counts the number of ions received at those times, and sends this information as electronic ion measurement signals to the computing device 118. The computing device 118 processes the signals received from the ion detector 150 to produce raw multi-dimensional MS data associated with each different ion mass detected. For example, the MS data may be three-dimensional (3D) data, where three data points are associated each different ion mass (peak) detected, namely retention time, m/z, and abundance. In the present context, "raw" data are data that have not yet been processed by the data analyzer 190.

Figure 2:
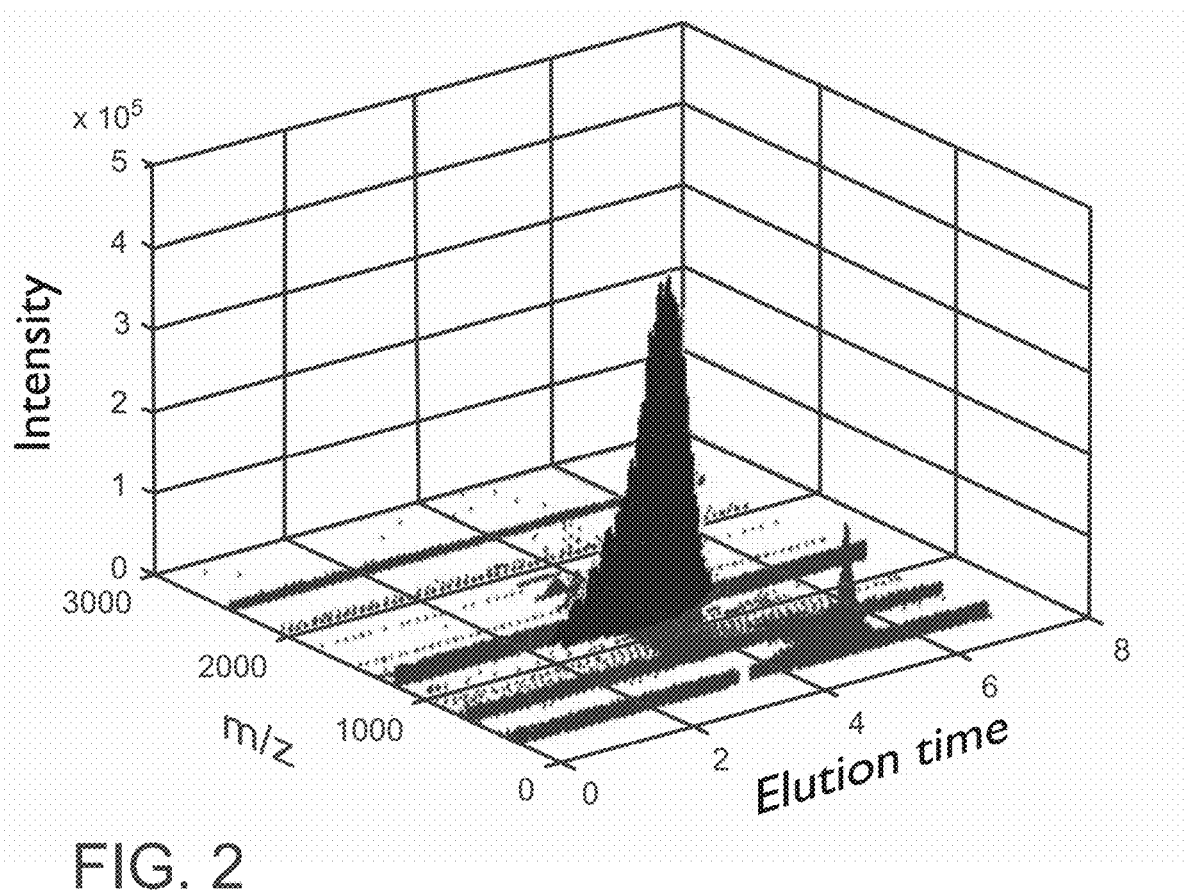
FIG. 2 is a plot (or set, or list) of an example of raw 3D LC/MS data acquired from a sample molecule.

As one non-exclusive example, FIG. 2 is a plot (or set, or list) of raw 3D LC/MS data acquired from a sample molecule. In the specific example, the raw 3D LC/MS data were acquired by running a sample through an LC instrument as the analytical separation instrument 138 and subsequently through the mass spectrometer portion of the MS system 100, and then transmitting the detector output to the computing device 118 for further processing as described above and illustrated in FIG. 1A. The set of data shown in FIG. 2 may be stored in a memory of the computing device 118, and then transferred to a memory of the data analyzer 190 such as the memory 164 shown in FIG. 1B. FIG. 2 is a graphical illustration of the set of data. FIG. 2 may also correspond to a display of the data, such as may be provided at a user output 170 (FIG. 1B) such as the display screen of the data analyzer 190 (or computing device 118).

In FIG. 2, the raw 3D LC/MS data are presented as a 3D plot defined by two horizontal axes and one vertical axis. The dimensions of the two horizontal axes are elution (retention) time (in minutes, or min) and m/z, respectively. The dimension of the vertical axis is ion signal intensity or ion abundance (in total number of ion counts). The values for m/z, elution time, and intensity are molecular features, i.e., features of the molecule from which the 3D LC/MS data were acquired.

Figure 3:
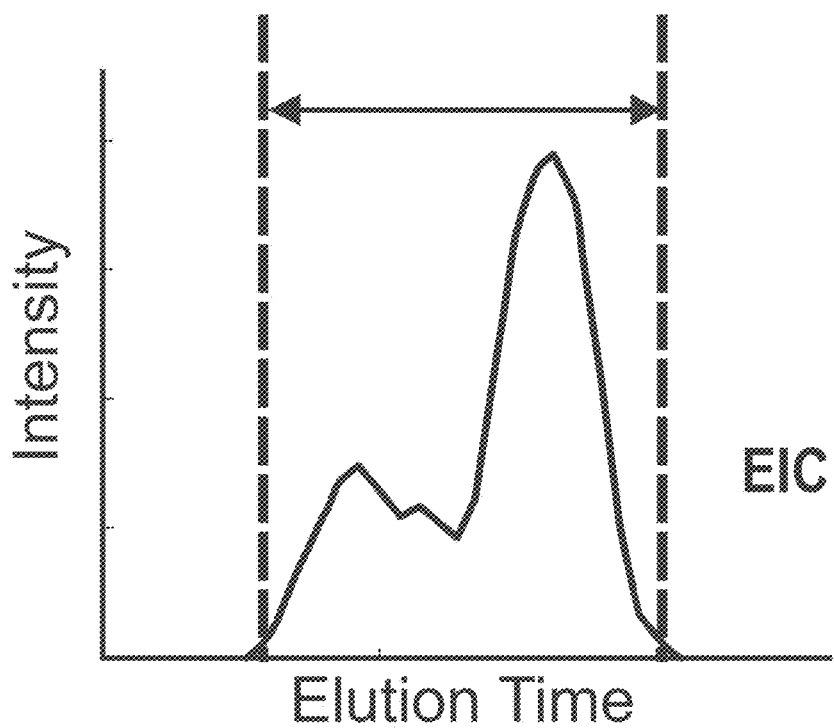
FIG. 3 is a schematic view of an example of an extracted ion chromatogram (EIC) as an example of a plot (or set, or list) of 2D data that may be extracted from the 3D LC/MS data illustrated in FIG. 2.

For any given elution time, a 2D plot (or set, or list) of intensity vs. m/z, i.e. a mass spectrum, can be extracted from the 3D LC/MS data. For any given m/z, a 2D plot (or set, or list) of intensity vs. elution time, i.e. a chromatogram, can be extracted from the same 3D LC/MS data. Extracted data sets may be utilized in algorithms that may be part of the methods disclosed herein. As one non-exclusive example, FIG. 3 illustrates an extracted ion chromatogram (EIC) as an example of a plot (or set, or list) of 2D data that may be extracted from the 3D LC/MS data illustrated in FIG. 2. The vertical axis corresponds to the intensity axis shown in FIG. 2. The horizontal axis corresponds to the elution time axis. As indicated by the vertical dashed lines and horizontal double-headed arrow in FIG. 3, the EIC may be filtered to include data only in a selected elution time span for a specific m/z range or ranges.

Once the raw MS data have been acquired, they may be analyzed by the data analyzer 190 to search for and identify molecules of the sample under analysis. In an embodiment, the data analyzer 190 is configured to perform stable label isotope tracing. The isotope tracing may be utilized to track an isotope as it proceeds through a chemical reaction or a biological reaction such as a metabolic pathway (e.g., metabolic flux analysis or MFA).

Figure 4:
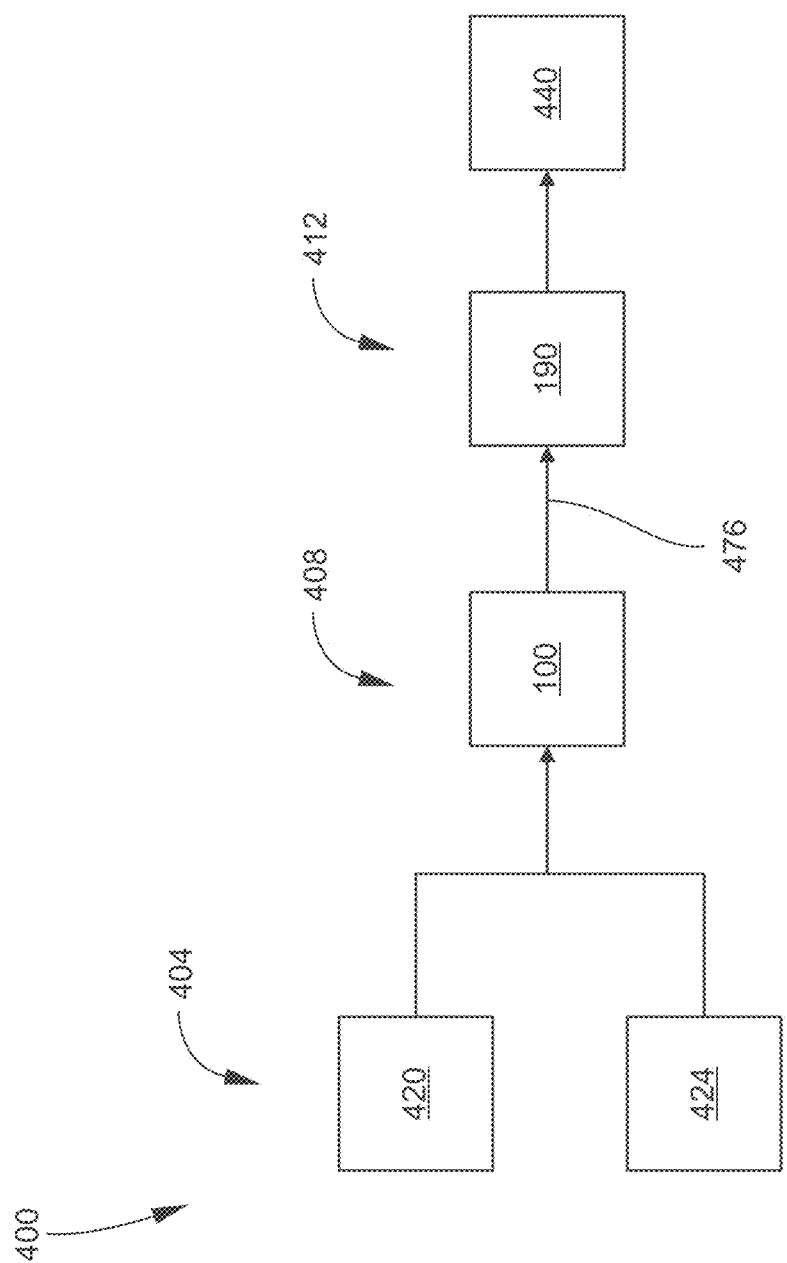
FIG. 4 is a schematic diagram of an example of a workflow 400 for data acquisition and analysis of samples involving stable label isotope tracing according to the present disclosure.

FIG. 4 is a schematic diagram of an example of a workflow 400 for data acquisition and analysis of samples involving stable label isotope tracing according to the present disclosure. Generally, the workflow 400 entails, in sequential order, a sample preparation stage 404, a sample processing and analysis stage 408, and a data processing and analysis stage 412.

During the sample preparation stage 404, an unlabeled sample 420 and an isotopically labeled sample 424 are prepared. The samples 420 and 424 may be chemical (non-biological) samples or biological samples. The unlabeled sample 420 includes compounds that have not been deliberately labeled with an isotope. In the present context, unlabeled compounds are either completely free of isotopes or include naturally occurring (natural abundance) isotopes. The labeled sample 424 includes at least one compound that has been isotopically labeled. The isotopically labeled sample 424 may be prepared by treating the initially unlabeled sample with a reagent or media containing the isotope of interest, after which the isotope becomes incorporated into a compound of the initially unlabeled sample. Isotopes typically utilized include, but are not limited to, carbon-13 ($^{13}C$), nitrogen-15 ($^{15}N$) and deuterium ($^{2}H$). Other than the isotopic enrichment, the isotopically labeled sample 424 is chemically or biologically equivalent to the unlabeled sample 420. In the present context, "chemically equivalent" means the stable label incorporation version of a chemical sample is a replication of the unlabeled version of the sample with one or more unlabeled compounds replaced by a stable label compound. Also in the present context, "biologically equivalent" means the stable label incorporation version of a biological sample is a replication of the unlabeled version of the sample with one or more unlabeled compounds replaced by a stable label compound.

During the sample processing and analysis stage 408, the unlabeled sample 420 and the isotopically labeled sample 424 are each introduced and run through an MS system, such as the MS system 100 described above and illustrated in FIG. 1A. The MS system 100 produces raw MS data 476 corresponding to each peak detected, and transmits the raw MS data 476 to the data analyzer 190.

During the data processing and analysis stage 412, the data analyzer 190 receives the raw MS data 476 from the MS system 100 or another source where the MS data 476 may have been stored, and processes and analyzes the raw MS data 476 according to methods described herein. For example, the data analyzer 190 may extract features from the raw MS data 476, analyze the features (e.g., perform a statistical analysis, pathway analysis, etc.), identify features as compounds, and identify and group isotopologues of the identified compounds. From this analysis, the data analyzer 190 produces output data 440. The output data 440 may include a list of compounds identified as being present in the samples 420 and 424, and other information such as a list and grouping of isotopologues. A user may then utilize the output data 440 for further analysis and interpretation, such as determining the flux and pathway taken by an isotope through a reaction or reactions.

Figure 5:
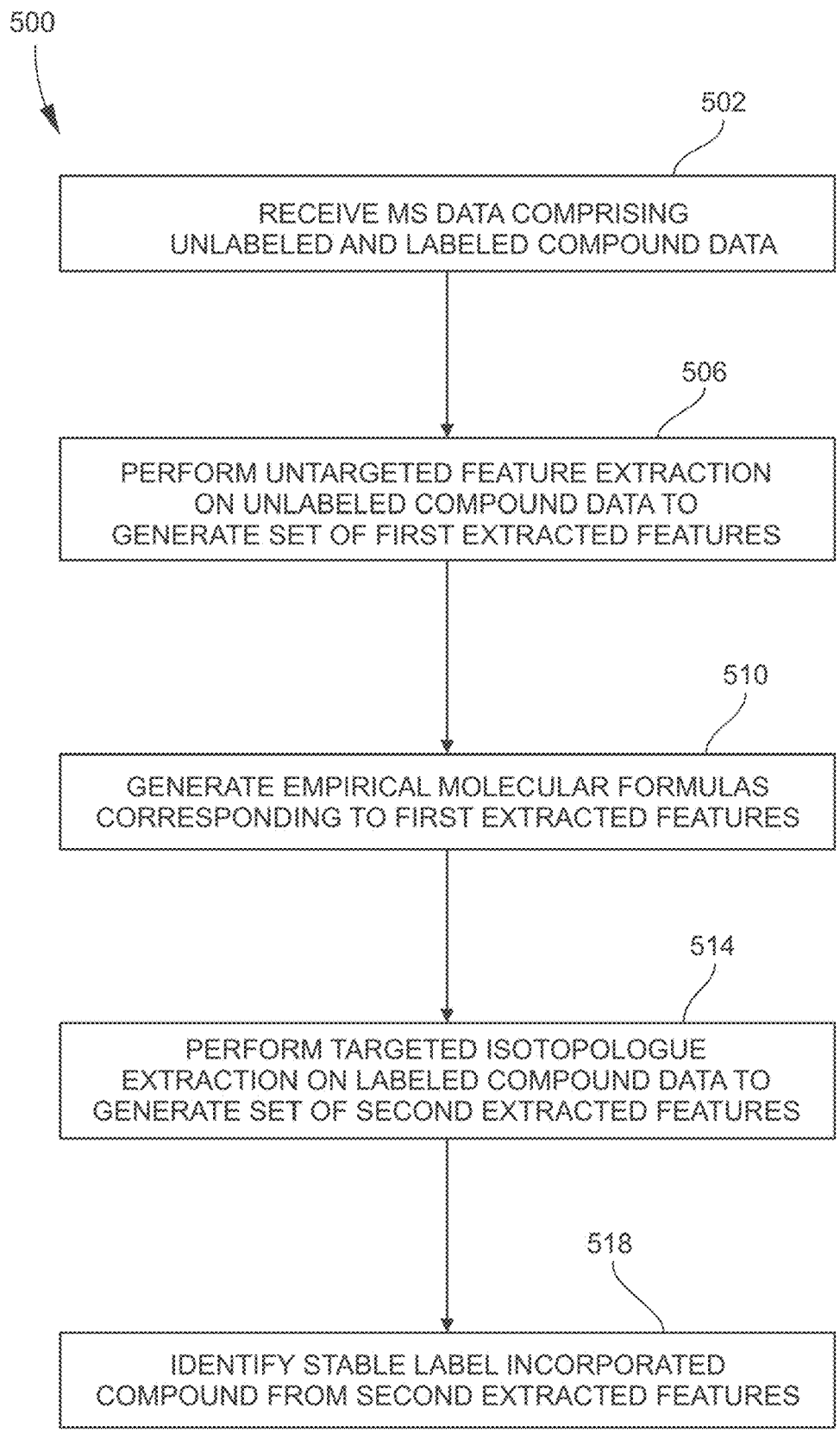
FIG. 5 is a flow diagram of an example of a method 500 for analyzing samples utilizing stable label isotope tracing according to the present disclosure.

FIG. 5 is a flow diagram 500 of an example of a method for analyzing samples utilizing stable label isotope tracing according to the present disclosure. The method 500 may be implemented, for example, by operating a data analyzer, such as the data analyzer 190 described herein and illustrated in FIGS. 1A and 1B. The method 500 may be implemented, for example, as part of a workflow such as the workflow 400 described above and illustrated in FIG. 4.

In the method, MS data is received (step 502), such as by the data analyzer 190. The MS data are data produced by an MS system such as the MS system 100 described herein, after the MS system is operated to perform untargeted data acquisition on a plurality of samples as described herein. In the present context, untargeted (or unbiased) data acquisition refers to a process in which data from all peaks detected by the MS system during the sample run are acquired and processed, not just from a limited number of known target compounds. The plurality of samples includes at least one unlabeled sample 420 containing unlabeled (chemical or biological) compounds and at least one labeled sample 424 containing isotopically labeled (chemical or biological) compounds, which are chemically or biologically equivalent to each other, as described above. The MS data includes unlabeled compound data and labeled compound data. The unlabeled compound data include retention time data, mass-to-charge ratio (m/z) data, and abundance data corresponding to molecular features of the unlabeled sample detected by the MS system, such as in the example shown in FIG. 2. Likewise, the labeled compound data include retention time data, m/z data, and abundance data corresponding to molecular features of the labeled sample detected by the MS system.

The samples 420 and 424 may be run sequentially through the MS system under the same operating conditions, instrument settings, etc. A desired number of replicates of each unlabeled sample 420 and each isotopically labeled sample 424 may be run through the MS system to generate the MS data.

After receiving the MS data, the data analyzer 190 performs untargeted feature extraction on the unlabeled compound data to generate a data set of first extracted features (step 506). The process of feature extraction utilized here is "untargeted" in that the features are extracted from all the unlabeled compound data that was acquired from the sample run. The data analyzer 190 may execute any suitable feature extraction algorithm that may be utilized for this purpose. One example is the Molecular Feature Extraction (MFE) algorithm available as part of the MASSHUNTER software, which is available from Agilent Technologies, Inc., Santa Clara, Calif., USA.

In an embodiment, the algorithm utilized for untargeted feature extraction may be configured to perform recursive feature extraction. In addition, one or more filtering techniques may be utilized to improve the results of the untargeted feature extraction. For example, a filtering technique may involve removing low-abundance features from the data set of first extracted features, where the low-abundance features have abundances (measured ion signal intensities) below a preset minimum threshold abundance value.

After generating the data set of first extracted features, the data analyzer 190 generates or calculates a plurality of empirical molecular formulas, respectively corresponding to the first extracted features (step 510). The generation of molecular formulas for the first extracted features may be done by utilizing a suitable algorithm, one example being the Molecular Formula Generation (MFG) algorithm available as part of the MassHunter Qualitative Analysis software, which is available from Agilent Technologies, Inc. As one example, the algorithm may be configured to assign the empirical molecular formulas to the corresponding first extracted features based on isotope pattern matching. Alternatively, the algorithm may be configured to assign the empirical molecular formulas to the corresponding first extracted features based on comparing the first extracted features to known compounds contained in an appropriate molecular formula database. One example is the Agilent-METLIN database available from Agilent Technologies, Inc. The use of a molecular formula database may yield more accurate molecular formulas, but assumes that the first extracted features correspond to known compounds. In either case, the generation of empirical formulas results in a feature list with retention times that may then be utilized as a target list from which features and their isotopologues may be extracted.

As another example, the empirical molecular formulas may be generated by executing a molecular formula generating algorithm configured to assign scores to the first extracted features, with higher scores indicating closer isotope pattern matching. The molecular formulas are assigned to the corresponding first extracted features having scores equal to or greater than preset a minimum threshold score. Low-scoring features (those having scores below the minimum threshold score) are removed from the data set of first extracted features.

In an embodiment, before the empirical molecular formulas are generated, retention-time alignment may be performed on the data set of first extracted features to ensure all found compounds are aligned correctly. For this purpose, the data analyzer 190 may allow the user to set a retention time window (e.g., in minutes) and a mass window (e.g., in parts per million or ppm, or daltons or Da).

In an embodiment, before performing targeted isotopologue extraction, unassigned features may be removed from the data set of first extracted features. Unassigned features are features with which molecular formulas could not be associated after executing the molecular formula generating algorithm.

After generating the empirical molecular formulas, the data analyzer 190 performs targeted isotopologue extraction on the labeled compound data to generate a data set of second extracted features (step 514). The targeted isotopologue extraction is based on the empirical molecular formula and retention time of each first extracted feature. The targeted isotopologue extraction may be performed by utilizing a suitable algorithm, one example being the Batch Isotopologue Extraction algorithm available as part of the above-noted MASSHUNTER software.

In an embodiment, after performing targeted isotopologue extraction, natural isotope abundance correction may be performed on the unlabeled compound data and the labeled compound data to improve accuracy in the identification of isotopologues. In addition, isotopic tracer purity correction may be performed on the labeled compound data to improve accuracy.

In an embodiment, after performing targeted isotopologue extraction, and preferably after performing any corrective techniques such as natural isotope abundance correction and isotopic tracer purity correction, the method may include removing first extracted features from the data set of first extracted features for which no isotopologues were identified, and removing second extracted features from the data set of second extracted features for which no isotopologues were identified After generating the data set of second extracted features, one or more stable label incorporated compounds are identified, i.e. it is determined that stable label incorporation has occurred, by observing changes in the isotopologue pattern from natural in the second extracted features—that is, by comparing an isotopologue pattern in the first extracted features to an isotopologue pattern in the second extracted features to determine whether there is a difference (in particular, a statistically significant difference) between the respective isotopologue patterns (step 518). For example, a (statistically significant) difference may be determined by evaluating the relative ratio heights of the different isotopologues.

In the present context, an isotopologue group consists of a base compound and all isotopologues of that base compound found in the sample under analysis.

The method may be utilized in a time-course manner to track the passage of an isotope through a reaction pathway in a reaction occurring in either a chemical or a biological sample, for example a metabolic pathway in the case of a biological sample. For this purpose, unlabeled and labeled samples may be extracted from their corresponding sample sources (e.g., a container containing a chemical mixture, a biological system such as a cell culture, etc.) at two or more succeeding points of time and run through the MS system to acquire data corresponding to the different time points. Steps 502-516 thus may be repeated one or more times, depending on the number of time points.

Accordingly, in an embodiment of the method, in a first iteration the unlabeled compounds and the isotopically labeled compounds are first unlabeled compounds and first isotopically labeled compounds, respectively, extracted from a sample source at a first-time point. First MS data are acquired from the first unlabeled compounds and the first isotopically labeled compounds by the MS system in the manner described above and illustrated in FIG. 5. Subsequently, second MS data are acquired, in the same manner, from second unlabeled compounds and second isotopically labeled compounds extracted from the sample source at a second time point subsequent to the first-time point. Additional iterations may be performed for additional time points as desired.

Figure 6A:
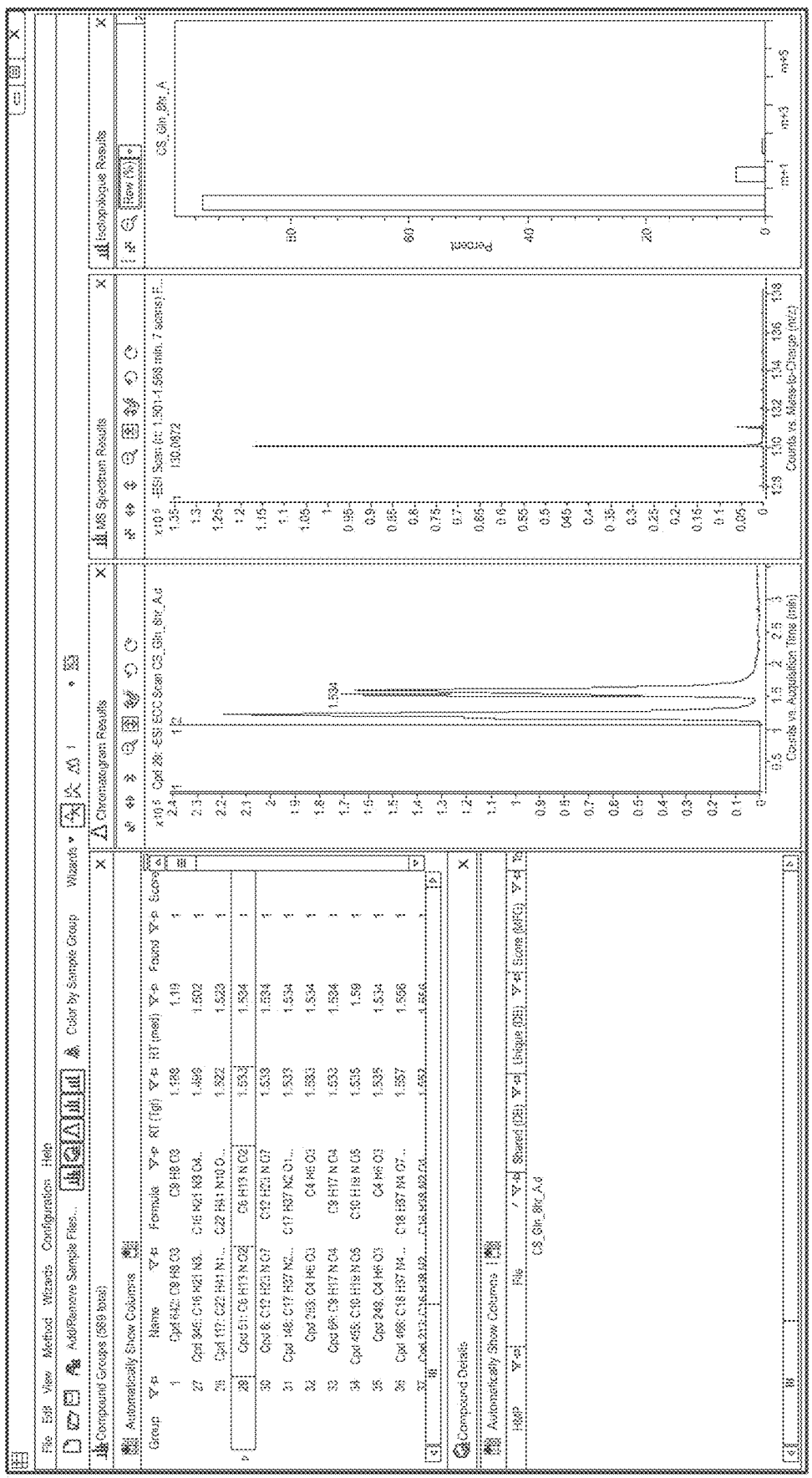
FIG. 6A is a screen shot illustrating an example of output data resulting of implementing the method for analyzing a sample according to the present disclosure.

FIG. 6A is a screen shot illustrating an example of output data resulting from implementing the method for analyzing a sample according to the present disclosure. The screen shot may be generated by a GUI provided by the data analyzer 190 or associated computing device. The screen shot includes several windows containing different types of output data. One window includes a list of compound groups found in the sample, with information for each compound group such as name, molecular formula, and retention time. One compound group (Group #29) has been selected by the user, as indicated by highlighting. Other windows may include data specific to the compound group selected, for example a chromatogram in counts (abundance, or signal intensity) versus acquisition (retention) time (in min), a mass spectrum in counts versus m/z (in m/z, or Da), and a histogram indicating the distribution by percentage (%) of isotopologues (m, m+1, m+2, et seq.) found for the selected compound group. FIG. 6A shows the results before natural abundance correction.

Figure 6B:
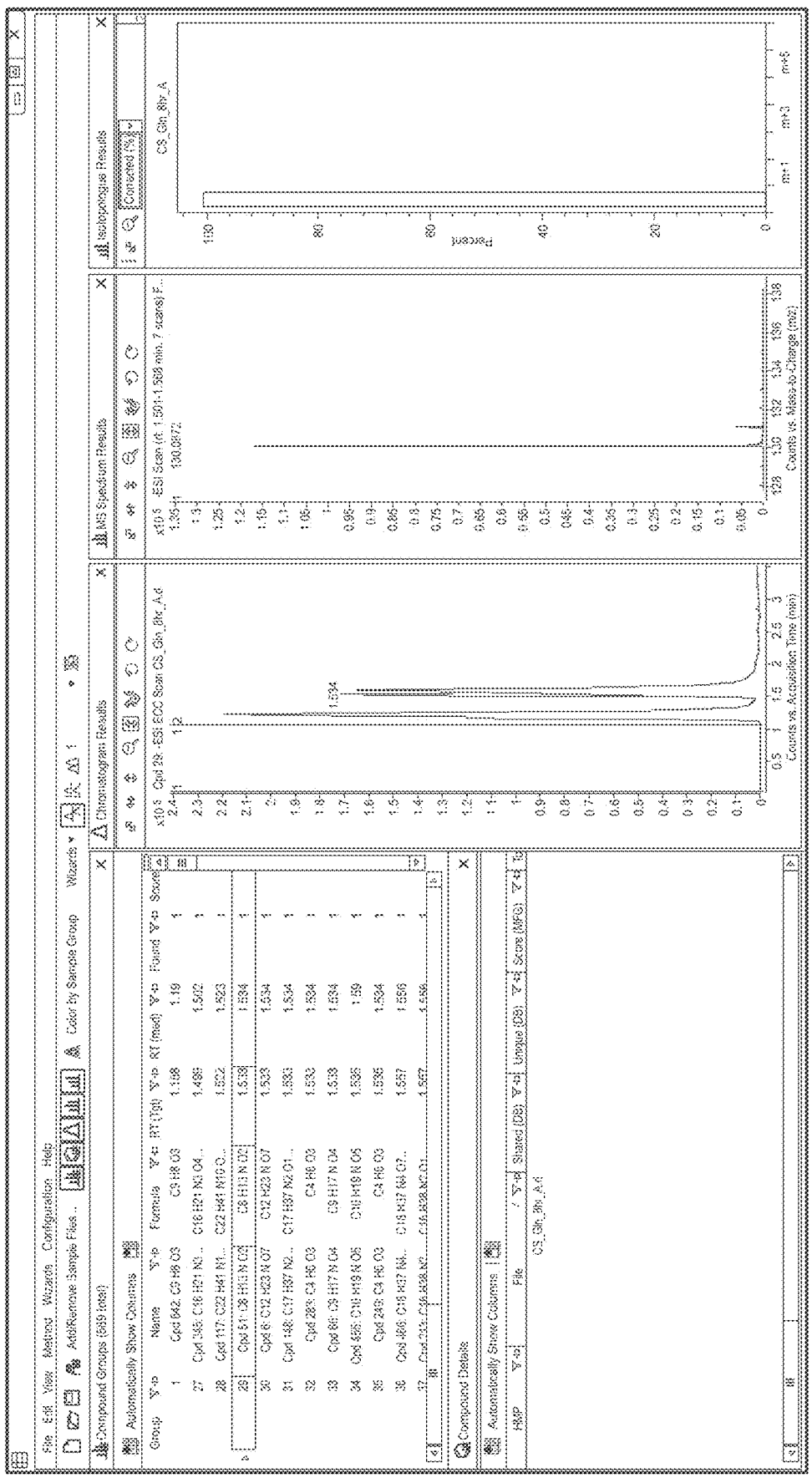
FIG. 6B is a screen shot similar to FIG. 6A, illustrating an example of output data resulting from the same experiment, but after natural abundance correction was performed.

By comparison, FIG. 6B is a screen shot similar to FIG. 6A, illustrating an example of output data resulting from the same experiment, but after natural abundance correction was performed. In the present example, after natural abundance correction, the isotopes corresponding to m+1 and m+2 have been removed from the isotopologue histogram.

Figure 7:
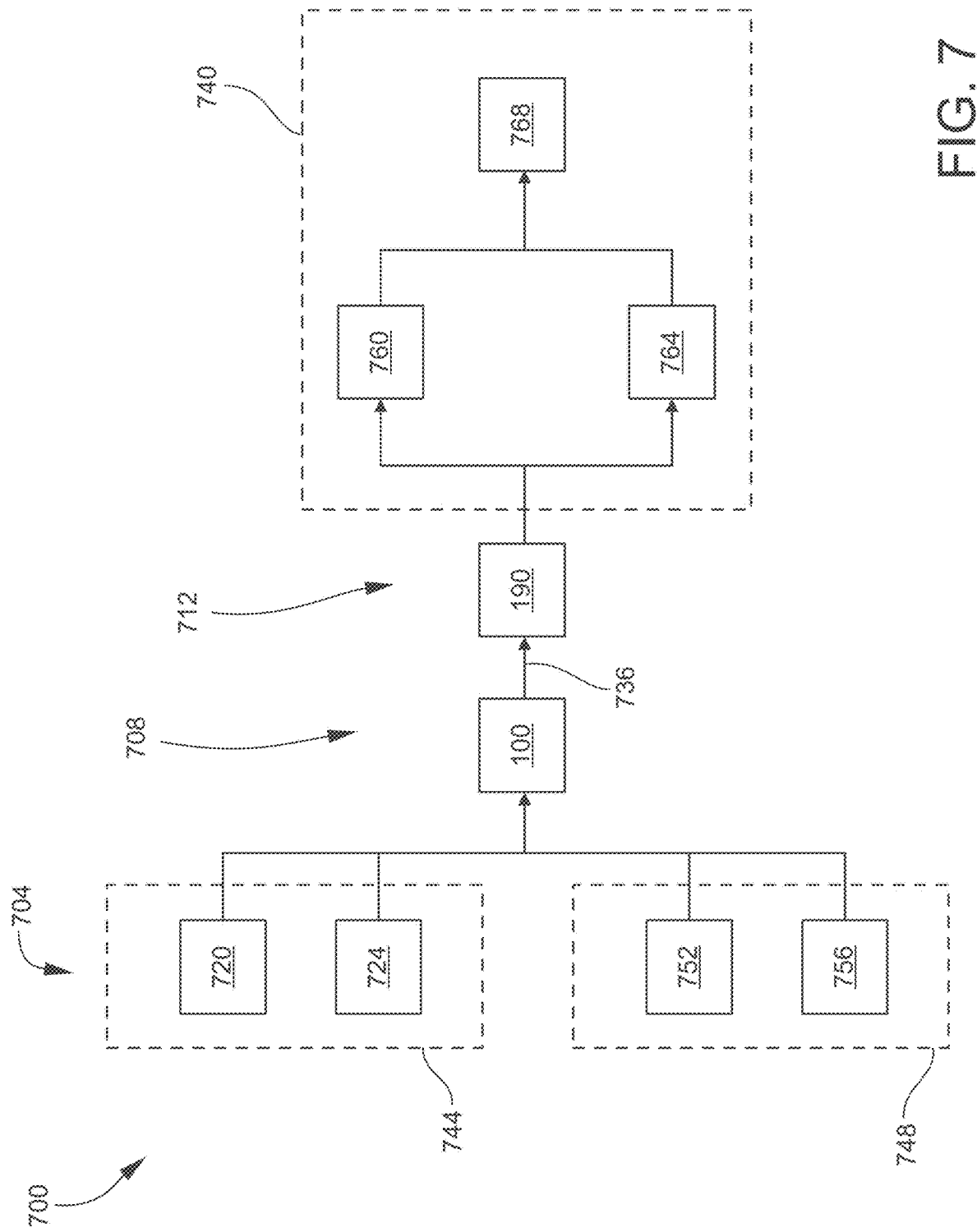
FIG. 7 is a schematic diagram of another example of a workflow 700 for data acquisition and analysis of samples involving stable label isotope tracing according to the present disclosure.

FIG. 7 is a schematic diagram of another example of a workflow 700 for data acquisition and analysis of samples involving stable label isotope tracing according to the present disclosure. In this example, the method entails performing a differential analysis to determine differences between control samples from a control sample source 744 and test samples from a test sample source 748. The sample sources 744 and 748 may be, for example, containers containing chemical mixtures, biological systems such as cell cultures, etc. The workflow 700 generally may be similar to the workflow 400 described above and illustrated in FIG. 4, thus entailing, in sequential order, a sample preparation stage 704, a sample processing and analysis stage 708, and a data processing and analysis stage 712.

During the sample preparation stage 704, an unlabeled control sample 720 and an isotopically labeled control sample 724 are prepared. In addition, an unlabeled test sample 752 and an isotopically labeled test sample 756 are prepared. The samples 720, 724, 752, and 756 are chemically or biologically equivalent to each other, except a desired isotope has been incorporated into compounds of the isotopically labeled control sample 724 and the isotopically labeled test sample 756 in the manner described above. In addition, the test samples 752 and 756 have been modified (e.g., perturbed, stimulated, challenged, etc.) in comparison to the control samples 720 and 724. That is, at least one chemical or biological condition of at least one compound of the test samples 752 and 756 has been altered relative to the same chemical or biological condition of the same compound of the control samples 720 and 724. The type of alteration will depend on the experiment. Examples include, but are not limited to, the addition of a chemical reagent or a pathogen, electromagnetic irradiation, heat treatment, etc.

During the sample processing and analysis stage 708, the samples 720, 724, 752, and 756 are each introduced and run through an MS system, such as the MS system 100 described above and illustrated in FIG. 1A. The MS system 100 produces raw MS data 736 corresponding to each peak detected. The MS system 100 then transmits the raw MS data 736 to the data analyzer 190, or the MS data 736 is otherwise provided to the data analyzer 190, as described above.

During the data processing and analysis stage 712, the data analyzer 190 receives the raw MS data 736 from the MS system 100 or another source where the MS data 736 may have been stored, and processes and analyzes the raw MS data 736 according to methods described herein. The method may be generally similar to that described above and illustrated in FIG. 5. In the present embodiment, the data analyzer 190 extracts and analyzes features from the unlabeled control sample 720, the isotopically labeled control sample 724, the unlabeled test sample 752, and the isotopically labeled test sample 756. As a result, the data analyzer 190 produces output data 740. The output data 740 includes a set of output data 760 resulting from the analysis of the raw MS data 736 acquired from the control samples 720 and 724, and a set of output data 764 resulting from the analysis of the raw MS data 736 acquired from the test samples 752 and 756. In the present embodiment, the method further includes, after performing targeted isotopologue extraction, performing a differential analysis 768 to determine a (statistically significant) difference between one or more isotope patterns of the unlabeled control sample 720 and labeled control sample 724 and one or more isotope patterns of the unlabeled test sample 752 and labeled test sample 756. The differential analysis 768 (e.g., the output data produced from the differential analysis 768) may be utilized to determine, for example, the effects of the altered condition on a compound of interest found in the samples 720, 724, 752, and 756.

As mentioned in the background section of the present disclosure, known untargeted data analyzing techniques may operate slowly and produce erroneous results such as isotope gaps and incorrect isotope clustering, and may be unable to find isotope incorporations that are stochastic rather than continuous. By comparison, the method disclosed herein offers a practical way to look for stable label isotope incorporations in a quicker fashion and with a lower error rate, and to accurately find stochastic as well as continuous isotope incorporations. The improved performance achieved by the method disclosed herein is due in part to the method's ability to convert the unlabeled data to empirical formulas, which are then utilized to mine the labeled data. Moreover, the method is effective even if the empirical formula generated is not an exact match for the true compound, as calculating an empirical formula using the mass values and isotope ratios of the compound spectra confines the empirical formula to a set of very similar empirical formulas.

Methods for analyzing a sample such as described above and illustrated in the Figures may be performed (carried out), for example, in a system that includes a processor and a memory as may be embodied in, for example, a data analyzer or computing device. A spectrometry system such as described above and illustrated in FIG. 1A may include, or be part of, or communicate with a system for analyzing a sample. As used herein, the term "perform" or "carry out" may encompass actions such as controlling and/or signal or data transmission. For example, a computing device such as illustrated in FIGS. 1A and 1B, or a processor thereof, may perform a method step by controlling another component involved in performing the method step. Performing or controlling may involve making calculations, or sending and/or receiving signals (e.g., control signals, instructions, measurement signals, parameter values, data, etc.).

As used herein, an "interface" or "user interface" is generally a system or device by which users interact with a computing device. An interface may include an input (e.g., a user input device) for allowing users to manipulate a computing device, and may include an output (e.g., a user output device) for allowing the system to present information and/or data, indicate the effects of the user's manipulation, etc. An example of an interface on a computing device includes a graphical user interface (GUI) that allows users to interact with programs in more ways than typing. A GUI typically may offer display objects, and visual indicators, as opposed to (or in addition to) text-based interfaces, typed command labels or text navigation to represent information and actions available to a user. For example, an interface may be a display window or display object, which is selectable by a user of a computing device for interaction. The display object may be displayed on a display screen of a computing device and may be selected by and interacted with by a user using the interface. In one non-limiting example, the display of the computing device may be a touch screen, which may display the display icon. The user may depress the area of the touch screen at which the display icon is displayed for selecting the display icon. In another example, the user may use any other suitable interface of a computing device, such as a keypad, to select the display icon or display object. For example, the user may use a track ball or arrow keys for moving a cursor to highlight and select the display object.

Exemplary Embodiments

Exemplary embodiments provided in accordance with the presently disclosed subject matter include, but are not limited to, the following:

1. A method for analyzing samples utilizing stable label isotope tracing, the method comprising: (a) receiving mass spectrometry (MS) data generated by an MS system performing untargeted data acquisition on a plurality of samples, wherein: the plurality of samples comprise an unlabeled sample containing unlabeled compounds, and a labeled sample containing isotopically labeled compounds and being chemically or biologically equivalent to the unlabeled sample; the MS data comprise unlabeled compound data and labeled compound data; the unlabeled compound data comprise retention time data, mass-to-charge ratio (m/z) data, and abundance data corresponding to molecular features of the unlabeled sample detected by the MS system; and the labeled compound data comprise retention time data, m/z data, and abundance data corresponding to molecular features of the labeled sample detected by the MS system; (b) performing untargeted feature extraction on the unlabeled compound data to generate a data set of first extracted features; (c) generating a plurality of empirical molecular formulas respectively corresponding to the first extracted features; (d) performing targeted isotopologue extraction on the labeled compound data to generate a data set of second extracted features, wherein the targeted isotopologue extraction is based on the empirical molecular formula and retention time of each first extracted feature; and (e) identifying a stable label incorporated compound by comparing an isotopologue pattern in the first extracted features to an isotopologue pattern in the second extracted features to determine whether there is a difference between the respective isotopologue patterns.

2. The method of embodiment 1, wherein the unlabeled compounds and the isotopically labeled compounds are non-biological compounds.

3. The method of embodiment 1, wherein the unlabeled compounds and the isotopically labeled compounds are biological compounds.

4. The method of any of the preceding embodiments, wherein the MS data is selected from the group consisting of: chromatography/MS data; and capillary electrophoresis/MS data.

5. The method of any of the preceding embodiments, wherein the receiving is done at a computing device comprising a processor and a memory.

6. The method of any of the preceding embodiments, wherein performing untargeted feature extraction on the unlabeled compound data comprises performing recursive feature extraction.

7. The method of any of the preceding embodiments, comprising, before generating the plurality of empirical molecular formulas, removing low-abundance features from the data set of first extracted features, wherein the low-abundance features have abundances below a minimum threshold abundance value.

8. The method of any of the preceding embodiments, comprising, before generating the plurality of empirical molecular formulas, performing retention-time alignment on the data set of first extracted features.

9. The method of any of the preceding embodiments, wherein generating a plurality of empirical molecular formulas comprises a step selected from the group consisting of: executing a molecular formula generating algorithm configured to assign the empirical molecular formulas to the corresponding first extracted features based on isotope pattern matching; and executing a molecular formula generating algorithm configured to assign the empirical molecular formulas to the corresponding first extracted features based on comparing the first extracted features to known compounds contained in a database.

10. The method of embodiment 9, comprising, before performing targeted isotopologue extraction, removing unassigned features from the data set of first extracted features, wherein the unassigned features are features with which molecular formulas could not be associated after executing the molecular formula generating algorithm.

11. The method of any of the preceding embodiments, wherein generating a plurality of empirical molecular formulas comprises: executing a molecular formula generating algorithm configured to assign scores to the first extracted features, with higher scores indicating closer isotope pattern matching; assigning the empirical molecular formulas to the corresponding first extracted features having scores equal to or greater than a minimum threshold score; and removing low-scoring features from the data set of first extracted features, wherein the low-scoring features have scores below the minimum threshold score.

12. The method of any of the preceding embodiments, comprising, after performing targeted isotopologue extraction, performing natural isotope abundance correction on the unlabeled compound data and the labeled compound data.

13. The method of any of the preceding embodiments, wherein the labeled sample was prepared by applying an isotopic tracer to the labeled sample, and the method further comprises, after performing targeted isotopologue extraction, performing isotopic tracer purity correction on the labeled compound data.

14. The method of any of the preceding embodiments, comprising, after performing targeted isotopologue extraction, removing first extracted features from the data set of first extracted features for which no isotopologues were identified, and removing second extracted features from the data set of second extracted features for which no isotopologues were identified.

15. The method of any of the preceding embodiments, wherein: the unlabeled compounds and the isotopically labeled compounds are first unlabeled compounds and first isotopically labeled compounds, respectively, extracted from a sample source at a first time point; the MS data are first MS data acquired from the first unlabeled compounds and the first isotopically labeled compounds; and the method further comprises repeating steps (a)-(e) using second MS data acquired from second unlabeled compounds and second isotopically labeled compounds extracted from the sample source at a second time point subsequent to the first time point.

16. The method of embodiment 15, wherein the sample source is a biological system, the first unlabeled compounds and the first isotopically labeled compounds are first metabolites, and the second unlabeled compounds and the second isotopically labeled compounds are second metabolites.

17. The method of embodiment, wherein: the unlabeled sample is an unlabeled control sample, the labeled sample is a labeled control sample, the first extracted features are first extracted features of the unlabeled control sample, and the second extracted features are second extracted features of the labeled control sample; the plurality of samples further comprise an unlabeled test sample and a labeled test sample chemically or biologically equivalent to the unlabeled control sample and the labeled control sample, and having a chemical or biological condition altered relative to the chemical or biological condition of the unlabeled control sample and the labeled control sample; and the method further comprises performing steps (a)-(e) on the unlabeled test sample and the labeled test sample to generate a data set of extracted features of the unlabeled test sample and extracted features of the labeled test sample.

18. The method of embodiment 17, comprising, after performing targeted isotopologue extraction, performing a differential analysis to determine a difference between an isotope pattern of the unlabeled control sample and the labeled control sample and an isotope pattern of the unlabeled test sample and the labeled test sample.

19. The method of embodiment 17 or 18, wherein the unlabeled control sample, the labeled control sample, the unlabeled test sample, and the labeled test sample include metabolites.

20. The method of any of the preceding embodiments, comprising acquiring the MS data by processing the sample in an MS system.

21. A system for analyzing a sample, comprising: a controller configured to receive MS data and control or perform all or part of the steps of the method of any of the preceding embodiments.

22. A non-transitory computer-readable medium, comprising instructions stored thereon, that when executed on a processor, control or perform the method of any of the preceding embodiments.

23. A system comprising the computer-readable storage medium of embodiment 22.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the computing device 118 or data analyzer 190 schematically depicted in FIGS. 1A and 1B. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the computing device 118 or data analyzer 190 in FIGS. 1A and 1B), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program may be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for analyzing samples utilizing stable label isotope tracing, the method comprising:
   (a) generating, by a mass spectrometry (MS) system, MS data by performing untargeted data acquisition on a plurality of samples,
   wherein:
      the plurality of samples comprise an unlabeled sample containing unlabeled compounds, and a labeled sample containing isotopically labeled compounds and being chemically or biologically equivalent to the unlabeled sample;
      the MS data comprise unlabeled compound data and labeled compound data;
      the unlabeled compound data comprise retention time data, mass-to-charge ratio (m/z) data, and abundance data corresponding to molecular features of the unlabeled sample detected by the MS system; and
      the labeled compound data comprise retention time data, m/z data, and abundance data corresponding to molecular features of the labeled sample detected by the MS system;
   (b) performing untargeted feature extraction on the unlabeled compound data to generate a data set of first extracted features;
   (c) generating a plurality of empirical molecular formulas respectively corresponding to the first extracted features;
   (d) performing targeted isotopologue extraction on the labeled compound data to generate a data set of second extracted features, wherein the targeted isotopologue extraction is based on the empirical molecular formula and retention time of each first extracted feature; and
   (e) identifying a stable label incorporated compound by comparing an isotopologue pattern in the first extracted features to an isotopologue pattern in the second extracted features to determine whether there is a difference between the respective isotopologue patterns.

2. The method of claim 1, wherein the unlabeled compounds and the isotopically labeled compounds are non-biological compounds.

3. The method of claim 1, wherein the unlabeled compounds and the isotopically labeled compounds are biological compounds.

4. The method of claim 1, wherein the MS data is selected from the group consisting of: chromatography/MS data; and capillary electrophoresis/MS data.

5. The method of claim 1, wherein performing untargeted feature extraction on the unlabeled compound data comprises performing recursive feature extraction.

6. The method of claim 1, comprising, before generating the plurality of empirical molecular formulas, removing low-abundance features from the data set of first extracted features, wherein the low-abundance features have abundances below a minimum threshold abundance value.

7. The method of claim 1, comprising, before generating the plurality of empirical molecular formulas, performing retention-time alignment on the data set of first extracted features.

8. The method of claim 1, wherein generating a plurality of empirical molecular formulas comprises a step selected from the group consisting of:
   executing a molecular formula generating algorithm configured to assign the empirical molecular formulas to the corresponding first extracted features based on isotope pattern matching; and
   executing a molecular formula generating algorithm configured to assign the empirical molecular formulas to the corresponding first extracted features based on comparing the first extracted features to known compounds contained in a database.

9. The method of claim 8, comprising, before performing targeted isotopologue extraction, removing unassigned features from the data set of first extracted features, wherein the unassigned features are features with which molecular formulas could not be associated after executing the molecular formula generating algorithm.

10. The method of claim 1, wherein generating a plurality of empirical molecular formulas comprises:
   executing a molecular formula generating algorithm configured to assign scores to the first extracted features, with higher scores indicating closer isotope pattern matching;
   assigning the empirical molecular formulas to the corresponding first extracted features having scores equal to or greater than a minimum threshold score; and
   removing low-scoring features from the data set of first extracted features, wherein the low-scoring features have scores below the minimum threshold score.

11. The method of claim 1, comprising, after performing targeted isotopologue extraction, performing natural isotope abundance correction on the unlabeled compound data and the labeled compound data.

12. The method of claim 1, wherein the labeled sample was prepared by applying an isotopic tracer to the labeled sample, and the method further comprises, after performing targeted isotopologue extraction, performing isotopic tracer purity correction on the labeled compound data.

13. The method of claim 1, comprising, after performing targeted isotopologue extraction, removing first extracted features from the data set of first extracted features for which no isotopologues were identified, and removing second extracted features from the data set of second extracted features for which no isotopologues were identified.

14. The method of claim 1, wherein:
the unlabeled compounds and the isotopically labeled compounds are first unlabeled compounds and first isotopically labeled compounds, respectively, extracted from a sample source at a first time point;
the MS data are first MS data acquired from the first unlabeled compounds and the first isotopically labeled compounds; and
the method further comprises repeating steps (a)-(e) using second MS data acquired from second unlabeled compounds and second isotopically labeled compounds extracted from the sample source at a second time point subsequent to the first time point.

15. The method of claim 14, wherein the sample source is a biological system, the first unlabeled compounds and the first isotopically labeled compounds are first metabolites, and the second unlabeled compounds and the second isotopically labeled compounds are second metabolites.

16. The method of claim 1, wherein:
the unlabeled sample is an unlabeled control sample, the labeled sample is a labeled control sample, the first extracted features are first extracted features of the unlabeled control sample, and the second extracted features are second extracted features of the labeled control sample;
the plurality of samples further comprise an unlabeled test sample and a labeled test sample chemically or biologically equivalent to the unlabeled control sample and the labeled control sample, and having a chemical or biological condition altered relative to the chemical or biological condition of the unlabeled control sample and the labeled control sample; and
the method further comprises performing steps (a)-(e) on the unlabeled test sample and the labeled test sample to generate a data set of extracted features of the unlabeled test sample and extracted features of the labeled test sample.

17. The method of claim 16, comprising, after performing targeted isotopologue extraction, performing a differential analysis to determine a difference between an isotope pattern of the unlabeled control sample and the labeled control sample and an isotope pattern of the unlabeled test sample and the labeled test sample.

18. The method of claim 16, wherein the unlabeled control sample, the labeled control sample, the unlabeled test sample, and the labeled test sample include metabolites.

19. A non-transitory computer-readable medium, comprising instructions stored thereon, that when executed on a processor, control or perform the method of claim 1.

20. A system comprising:
a mass spectrometry (MS) system;
at least one processor;
a memory storing machine readable instructions that, when executed by the at least one processor, cause the at least one processor to:
generate, by the MS system, MS data by performing untargeted data acquisition on a plurality of samples, wherein:
the plurality of samples comprise an unlabeled sample containing unlabeled compounds, and a labeled sample containing isotopically labeled compounds and being chemically or biologically equivalent to the unlabeled sample;
the MS data comprise unlabeled compound data and labeled compound data;
the unlabeled compound data comprise retention time data, mass-to-charge ratio (m/z) data, and abundance data corresponding to molecular features of the unlabeled sample detected by the MS system; and
the labeled compound data comprise retention time data, m/z data, and abundance data corresponding to molecular features of the labeled sample detected by the MS system;
perform untargeted feature extraction on the unlabeled compound data to generate a data set of first extracted features;
generate a plurality of empirical molecular formulas respectively corresponding to the first extracted features;
perform targeted isotopologue extraction on the labeled compound data to generate a data set of second extracted features, wherein the targeted isotopologue extraction is based on the empirical molecular formula and retention time of each first extracted feature; and
identify a stable label incorporated compound by comparing an isotopologue pattern in the first extracted features to an isotopologue pattern in the second extracted features to determine whether there is a difference between the respective isotopologue patterns.

* * * * *